(12) United States Patent
Calton et al.

(10) Patent No.: US 6,180,127 B1
(45) Date of Patent: Jan. 30, 2001

(54) SLOW RELEASE INSECT REPELLENTS

(75) Inventors: Gary J. Calton, Elkridge, MD (US); Sidney R. Siemer, Fresno, CA (US); Louis L. Wood, Rockville, MD (US)

(73) Assignee: AquaSource, Inc., Glen Burnie, MD (US)

( * ) Notice: Under 35 U.S.C. 154(b), the term of this patent shall be extended for 0 days.

(21) Appl. No.: 08/132,289

(22) Filed: Oct. 6, 1993

Related U.S. Application Data

(63) Continuation of application No. 07/899,367, filed on Jun. 16, 1992.

(51) Int. Cl.$^7$ ................................................. A01N 25/08
(52) U.S. Cl. ............................ 424/409; 424/45; 424/47; 424/76.3; 424/405; 424/78.03; 424/78.24; 424/78.36; 424/411; 514/919
(58) Field of Search ............................ 424/405, 47, 76.3, 424/45, 409, 78.03, 78.24, 78.36, 411; 514/919

(56) References Cited

U.S. PATENT DOCUMENTS

| | | | | |
|---|---|---|---|---|
| 2,435,005 | * | 1/1948 | Huppke et al. | 167/90 |
| 2,792,328 | * | 5/1957 | Socec | 163/24 |
| 2,808,359 | | 10/1957 | Schemtrier | 167/22 |
| 3,966,902 | * | 6/1976 | Chromecek | 424/59 |
| 4,241,048 | * | 12/1980 | Durbak et al. | 424/45 |
| 4,348,380 | * | 9/1982 | Jacquet et al. | 424/47 |
| 4,774,081 | | 9/1988 | Flashinski et al. | 424/78 |
| 4,774,082 | | 9/1988 | Flashinski et al. | 424/78 |
| 4,837,013 | * | 6/1989 | Login et al. | 424/70 |
| 4,894,222 | * | 1/1990 | Matravers | 424/59 |
| 5,002,762 | * | 3/1991 | Bolich, Jr. | 424/70 |
| 5,102,662 | * | 4/1992 | Gallagher | 424/409 |
| 5,139,770 | * | 8/1992 | Shih et al. | 424/59 |
| 5,145,675 | * | 9/1992 | Won | 424/78.31 |
| 5,173,303 | * | 12/1992 | Lay et al. | 429/450 |
| 5,204,090 | * | 4/1993 | Han | 424/59 |
| 5,221,535 | * | 6/1993 | Domb | 424/450 |
| 5,221,698 | * | 6/1993 | Amidon | 523/122 |
| 5,227,406 | * | 7/1993 | Beldock et al. | 515/703 |
| 5,290,570 | * | 3/1994 | Nichols | 424/499 |
| 5,292,503 | * | 3/1994 | Raleigh et al. | 424/59 |

FOREIGN PATENT DOCUMENTS

1029268 * 4/1978 (CA) .......................... 424/DIG. 10

OTHER PUBLICATIONS

Federal Register 56 (137) 32514–15, Jul. 17, 1991 EPA.*
Reifenrath, W.G. et al. Journal of Pharmaceutical Sciences vol. 71, No. 9, Sep. 1982, pp. 1041–1018. In vitro skin evaporation and penentration characteristics of mosquito repellents.
Reifenrath, W.G. et al. J. Amer. Mosquito Control. Assoc. vol. 5, Mar. 1989, pp. 45–51. Evaporation and skin penetration characteristics of mosquito repellent formulations.
Mehr, Z.A., et al. J. Am. Mosq. Control. Assoc. vol. 1, Jun. 1985, p. 143–147. Laboratory evaluation of controlled–release insect repellent formulations.
Lurie et al. (In Russian). Pharmacokinetics of insect repellent N,N–diethyl toluamide. Med. Parazitol, vol. 47, p. 72–77, 1979.
Oteri, R., et al. Cosmetics & Toiletries, vol. 102,107–109, 1987.
A new waterproofing agent for sunscreen products.
Chemical Abstracts vol. 110, 207847s 1989., Randen, N.A. Mosquito repellent compositions comprising an acrylic polymer.
Anonymous, Ganex WP–660 Resin, GAF Chemicals Corp, 1990, pp. 1–8, 2302–217 5M–1290.
Anonymous, Ganex Alkylated polyvinylpyrrolidones for personal care. p. 1–20, 1989, GAF Chemicals Corporation.
Henkel Corp. Empol Dimer and Polybasic Acids. Oct. 12, 1993.

* cited by examiner

Primary Examiner—Neil S. Levy
(74) Attorney, Agent, or Firm—William S. Ramsey

(57) ABSTRACT

This invention discloses slow release formulations for use in application of volatile insect repellents. A copolymer of polyvinyl pyrrolidone and an alkyl group of 4–30 carbons provides the slow release properties. The formulations are characterized by high residual action, low skin penetration, and high resistance to removal by water.

12 Claims, No Drawings

SLOW RELEASE INSECT REPELLENTS

This is a continuation of application Ser. No. 07/899,367, filed Jun. 16, 1992.

FIELD OF THE INVENTION

This invention relates to insect repellents, and in particular to insect repellent formulations having enhanced residual activity.

BACKGROUND OF THE INVENTION

Volatile insect repellents disappear relatively rapidly when applied to the skin. They are also quickly washed away by water, whether fresh or salt containing.

The most prominent insect repellent in use today is N,N'-diethyl toluamide, commonly known as DEET. Other volatile insect repellents are known including ethyl hexanediol; 2-(octylthio)ethanol; dimethyl phthalate; di-n-propyl-2,5-pyridine dicarboxylate; 1,5a,6,9,9a, 9b-hexahydro-4a(4b)-dibenzofuran carboxaldehyde; citronellal; citronellol; geraniol; nerol; and linalool. The formulation of such insect repellents is particularly problematic due to the greasy feel of many of the repellents and especially the effect of DEET in staining clothing, crazing plastics and washing away in humid or rainy weather or when the person using the repellent is participating in water sports such as swimming or fishing. In addition, the lack of retention of insect repellents due to the action of water is also affected by the individual wearer's sweating.

The evaporation of the insect repellent is directly related to the ambient temperature and wind velocity. Approximately 50% of a topically applied dose is absorbed in six hours with peak plasma levels being reached in 1 hour (Lurie et al, Pharmacokinetics of insect repellent N,N-diethyl toluamide. Med. Parazitol., 47, 72, 1979).

Mehr et al, (Laboratory Evaluation of Controlled-Release Insect Repellent Formulations, J. Am. Mosq. Control Assoc., 1,143, 1985) evaluated a number of controlled release formulations of microencapsulated DEET and hydrophilic vinyl polymers such as polyvinylpyrrolidone. The polyvinylpyrrolidone formula was no better than unformulated DEET in repelling mosquitoes.

Reifenrath et al, (Evaporation and Skin penetration characteristics of mosquito repellent formulations. J. Am. Mosq. Control Assoc., 5, 45 1989) tested silicone polymers, acrylate polymers, fatty acids and mixtures of repellents and evaluated evaporation and skin penetration. No differences in evaporation and skin penetration was found between formulations containing the polymers and unformulated DEET or with a mixture of dimethyl phthalate and DEET.

Reifenrath et al, (In vitro skin evaporation and penetration characteristics of mosquito repellents. J. Pharm. Sci. 71, 1014, 1982) showed that the duration of repellent efficacy on man correlated with the time that vapor levels at the surface of the skin exceeded the minimum effective evaporation rates in vitro.

U.S. Pat No. 4,474,081 discloses the use of maleic anhydride/alpha olefin polymers and terpolymers to provide slow release of contact insect repellents when applied to the surface of the skin.

U.S. Pat No. and U.S. Pat. No. 4,774,082 discloses the use of maleic anhydride/alpha olefin polymers and terpolymers to provide slow release of volatile insect repellents when applied to the surface of the skin.

Chemical Abstracts 110, 207847s (1989), discloses mosquito repellent compositions which have an active agent and an oil-soluble, water insoluble acrylate polymer comprising acrylic acid, stearyl methacrylate and isooctyl acrylate.

Ideally, an insect repellent formulation for mammalian use should be non-staining, non-greasy, long lasting, and resistant to washing off from rain, humidity, sweat, fresh waters or ocean waters and reduce penetration of the skin.

SUMMARY OF THE INVENTION

The composition of this invention comprises a copolymer of polyvinyl pyrrolidone and an alkyl group of 4–30 carbons formulated with an insect repellent.

The object of this invention is to provide an insect repellent composition having enhanced residual insect repellent activity comprising: (1) an alkylated polyvinylpyrrolidone; and (2) a volatile insect repellent.

Another object of this invention is to provide an insect repellent composition having enhanced resistance to removal by water, salt water or sweat comprising: (1) an alkylated polyvinylpyrrolidone; and (2) a volatile insect repellent.

Yet another object of this invention is to provide an insect repellent composition having enhanced residual insect repellent activity comprising: (1) an alkylated polyvinylpyrrolidone; (2) a volatile insect repellent and (3) a silicone polymer.

Still another object of the invention is to provide a surface application of an odorant with improved residence time.

Another object of this invention is to provide a matrix containing an odorant which is capable of being sprayed or spread evenly.

Although a great deal of investigation into the cosmetic uses of alkylated polyvinylpyrrolidone copolymers has been carried out, their utility to serve as slow release agents for odorants such as perfumes and insect repellents has not been previously observed.

The compositions of the invention are completely unexpected to give residual activity of insect repellency in light of the previous art. This unexpected characteristic, combined with their known cosmetic appeal of non-greasy and water repellent formulations, provide ideal volatile insect repellent formulations.

DESCRIPTION OF THE PREFERRED EMBODIMENTS

Volatile insect repellents which are of value in this invention are those which have the combined characteristics of insect repellency and safety and which can be applied to mammalian skin.

The formulation of this invention contains an alkylated polyvinyl pyrrolidone copolymer and a volatile insect repellent. This formulation is characterized by high residual action, low skin penetration, and high resistance to removal by water. Other volatile materials such as fragrances may be formulated in the compositions of this invention. Such compositions are non-greasy and are easily applied to the skin.

By way of example and not by limitation, insect repellents which are valuable in the invention include: N,N'-diethyl toluamide, commonly known as DEET; ethyl hexanediol; 2-(octylthio)ethanol; dimethyl phthalate; di-n-propyl-2,5-pyridine dicarboxylate; 1,5a,6,9,9a, 9b-hexahydro-4a(4b)-dibenzofuran carboxaldehyde; citronellal; citronellol; geraniol; nerol; and linalool. Other insect repellents recognized in the art, may be used in this invention.

The concentrations of the repellent in the compositions of this invention may be varied, and are limited only by their presence in the composition in such quantities that they will provide effective relief from the targeted insect or insects to be repelled and the concentration of the other ingredients of the formulation.

Thus, the concentration of the insect repellent may be from 1 to 90%, however a range of 1 to 25% is preferred.

Alkylated polyvinylpyrrolidones which may be used include copolymers of polyvinylpyrrolidone and an alpha olefin of chain length of 4 to 30 carbons. Preferred embodiments of this invention are the hexadecene copolymer of polyvinylpyrrolidone (PVP), the eicosene copolymer of PVP and the 1-triacontene copolymer of PVP.

The silicone polymers which are useful in the present invention include dimethicone (Dow Corning 200 Fluids), dimethicone and trimethylsiloxysilicate (Dow Corning 593 Fluid), stearoxy dimethicone (SWS 755 Wax), cyclomethicone (Dow Corning 344 or 345 Fluid, Union Carbide 7158 Fluid, GE SF 1173, 1202 or 1204), polysiloxane (Dow Corning 3225C Fluid), cyclomethicone and dimethicone (Dow Corning X2-1401) and dimethicone (GE SE30, 76 gums, ultrahigh molecular weight dimethicone) and mixtures thereof.

Silicone polymers which are preferred in the invention include polysiloxane (Dow Corning 3225C Fluid) and polydimethylcyclosiloxane (Dow 344 or 345 Fluid).

The silicone polymers may be present in the range of 1 to 60%.

Preservatives which are know in the art to be useful in the present invention include: Quaternium 15 (Dowicil 200), methyl paraben, propyl paraben, dihydroxydimethyl hydantoin, benzyl alcohol, methyl chloroisothiazolinone and methyl isothiazolinone, butyl paraben, imidazolidinyl urea, diazolidinyl urea, disodium ethylenediamine tetraacetic acid and tetrasodium ethylenediamine tetraacetic acid and mixtures thereof. The quantities of such agents used may vary depending on the combination and the levels required to prevent microbial growth.

Oils which are useful in the present invention may be present in the range of up to 50% of the composition of the present invention. A preferred range is up to 30%.

Other ingredients which are known in the art to be useful in the preparation of acceptable cosmetic formulations may also be included in the present invention to provide cosmetically acceptable formulations.

The following examples are given by way of illustration and not of limitation.

EXAMPLE 1

A formula containing low quantities of N,N'-diethyl-m-toluamide (DEET).

The following formula was prepared by heating the water in A to 85° C. with agitation and adding carbomer 940 (a trademark of B.F. Goodrich for acrylic acid, homopolymer). After the carbomer 940 was dissolved, the triethanolamine was added. In a separate container, a mixture, B, of dimethicone, glyceryl stearate SE, PVP/eicosene copolymer (Ganex V-220, a trademark of GAF), DEET and myristyl myristate was heated with stirring until the mixture was uniform. Mixtures A and B were added together with stirring and allowed to cool while continuing the stirring. At around 40° C., the mixture C, consisting of diazolidinyl urea, methylparaben and propylparaben in propylene glycol was added. The whole was cooled to room temperature with continued stirring.

| Formula | | parts added |
|---|---|---|
| A. Deionized water | | 87.3 |
| carbomer 940 | | 0.1 |
| triethanolamine, 98% | | 0.1 |
| B. dimethicone | | 1.0 |
| myristyl myristate | | 1.0 |
| PVP/eicosene copolymer | | 2.0 |
| glyceryl stearate SE | | 3.5 |
| DEET | | 4.0 |
| C. Contents below | | 1.0 |
| diazolidinyl urea | 30% | |
| methylparaben | 11% | |
| propylparaben | 3% | |
| propylene glycol | 56% | |

This material was equal in effectiveness of repelling mosquitoes to a 100% DEET solution at 1 hour.

EXAMPLE 2

A formula containing moderately high quantities of N,N'-diethyl-m-toluamide (DEET)

A mixture of cyclomethicone, cyclomethicone and dimethicone copolyol, DEET and PVP/polyeicosene copolymer were heated with stirring until the mixture was a homogeneous solution. At that time the solution was allowed to cool to room temperature.

| Contents | weight | % Concentration |
|---|---|---|
| DEET | 19.8 g | 19.8 |
| PVP/eicosene copolymer | 39.6 g | 39.6 |
| cyclomethicone | 26.4 g | 26.4 |
| cyclomethicone and dimethicone copolyol | 13.2 g | 13.2 |
| fragrance | 1.0 g | 1.0 |

Tests for effectiveness of mosquito repellant activity were conducted by using freshly pupated adult mosquitos caged such that a human volunteer's arm could be placed into the cage. Each volunteers arm was treated with a standard 90% DEET/10% alcohol solution and a formulation to be tested. Both materials were applied in approximately 2 inch circles, with both standard and formulation on the same arm. The volunteer's arm was covered in all areas not treated. Mosquito bites in each area were recorded for comparison and a percentage of protection was calculated per time of exposure based on bites recorded on a non-treated area of the volunteer's other arm.

This formula was equal in efficacy to that of the 100% DEET solution.

To qualitatively determine skin penetration, a human volunteer, known to be sensitive to DEET, was blindfolded and comparative solutions were placed on the volar forearm. The volunteer was asked to identify the solution containing DEET, compared to a known DEET solution or a non-DEET solution. The burning sensation was found to be clearly indicative of DEET at a level of 2% or above in the formulation.

This formula was superior in lack of skin penetration as indicated by no reaction in the human volunteer.

EXAMPLE 3

A formula containing high quantities of N,N'-diethyl-m-toluamide (DEET)

A mixture of cyclomethicone, cyclomethicone and dimethicone copolyol, DEET, PVP/polyeicosene copolymer and fragrance were heated with stirring until the mixture was a homogeneous solution. At that time the solution was allowed to cool to room temperature.

| Contents | weight | % Concentration |
|---|---|---|
| DEET | 40.0 g | 40.0 |
| PVP/eicosene copolymer | 20.0 g | 20.0 |
| cyclomethicone | 26.7 g | 26.7 |
| cyclomethicone and dimethicone copolyol | 12.3 g | 12.3 |
| fragrance | 1.0 g | 1.0 |

Tests for effectiveness of mosquito repellant activity were conducted by using freshly pupated adult mosquitos caged such that a human volunteer's arm could be placed into the cage. Each volunteer's arm was treated with a standard 90% DEET/10% alcohol solution and a formulation to be tested. Both materials were applied in approximately 2 inch circles, with both standard and formulation on the same arm. The volunteer's arm was covered in all areas not treated. Mosquito bites in each area were recorded for comparison and a percentage of protection was calculated per time of exposure based on bites recorded on a non-treated area of the volunteer's other arm.

This formula was equal in efficacy to that of the 100% DEET solution.

To qualitatively determine skin penetration, a human volunteer, known to sensitive to DEET, was blindfolded and comparative solutions were placed on the volar forearm. The volunteer was asked to identify the solution containing DEET, compared to a known DEET solution or a non-DEET solution. The burning sensation was found to be clearly indicative of DEET at a level of 2% or above in the formulation.

This formula was superior in lack of skin penetration as indicated by no reaction in the human volunteer.

EXAMPLE 4

A formula containing medium quantities of DEET.

The following ingredients were placed in a container and heated with stirring to 80° C. and then cooled to room temperature while continuing to stir.

| Contents | weight | % Concentration |
|---|---|---|
| 1% hydroxypropyl cellulose in water | 12,000 g | 73.3 |
| glycerol | 857 g | 5.2 |
| DEET | 429 g | 2.6 |
| Pluronic L-64 (a surfactant made by BASF) | 242 g | 1.5 |
| PVP/eicosene copolymer (a product of GAF) | 857 g | 5.2 |
| cyclomethicone | 1114 g | 6.8 |
| cyclomethicone and dimethicone copolyol | 686 g | 4.1 |
| paraban solution (10% methyl and propylparabans in propylene glycol) | 171 g | 1.0 |

This formula was equal in efficacy to that of the 100% DEET solution in field conditions.

In the test described in Example 2, this formula was superior in lack of skin penetration as indicated by no reaction in the human volunteer.

EXAMPLE 5

A formula based on polyvinylpyrrolidone/1-triacontene copolymer.

The following ingredients were prepared and agitated with a propeller stirrer. Solution A was prepared and heated to 80° C. and then solution (B) was headed to 80° C. and added to Solution A. The mixture was allowed to cool to 40° C. and Solution C was added and the whole was allowed to cool to room temperature with continued agitation.

| | grams added |
|---|---|
| (A) Diisopropyl adipate | 8.5 |
| DEA-cetyl phosphate | 2.0 |
| polyvinylpyrrolidone/1-triacontene copolymer | 3.0 |
| dimethicone | 1.0 |
| DEET | 7.5 |
| (B) Deionized water | 70.0 |
| hydroxyethylcellulose | 0.3 |
| (C) methyl paraban/propyl paraban/ diazolidinyl urea in propylene glycol (1:1:2:6) | 1.0 |

This formula was equal in efficacy to that of the 100% DEET solution in field conditions.

In the test described in Example 2, this formula was superior in lack of skin penetration as indicated by no reaction in the human volunteer.

EXAMPLE 6

A formula based on polyvinylpyrrolidone/hexadecene copolymer.

The following ingredients were prepared and agitated with a propeller stirrer. Solution A was prepared and heated to 80° C. and then solution (B) was headed to 80° C. and added to Solution A. The mixture was allowed to cool to 40° C. and Solution C was added and the whole was allowed to cool to room temperature with continued agitation.

| | grams added |
|---|---|
| (A) sorbitan oleate | 0.4 |
| glyceryl stearate | 1.0 |
| polyvinylpyrrolidone/hexadecene copolymer | 3.0 |
| cetyl octanoate | 6.0 |
| DEA cetyl phosphate | 2.0 |
| DEET | 7.5 |
| (B) Deionized water | 76.0 |
| Carbopol 940 | 0.1 |
| Sorbitol | 5.0 |
| Cheelox BF-78 | 0.5 |
| after thorough mixing add | |
| triethanolamine | 0.1 |
| (C) methyl paraban/propyl paraban/ diazolidinyl urea in propylene glycol (1:1:2:6) | 1.0 |

This formula was equal in efficacy to that of the 100% DEET solution in field conditions.

In the test described in Example 2, this formula was superior in lack of skin penetration as indicated by no reaction in the human volunteer.

EXAMPLE 7

Aerosol formulations and ratios of insect repellent to polymer.

A mixture of DEET, PVP/eicosene copolymer and chloroform was prepared as shown in the table below. Absorbent paper sticks were dipped in the solution and placed in an oven at 36° C. with a light flow of air. The weights of material absorbed were determined by weighing the total quantity of solution before and after dipping the paper stick in the solution. The paper sticks were checked periodically for the presence of DEET odor. The results obtained are shown in the table.

| DEET (g) | PVP/ eicosene (g) | chloro- form (g) | repellent/ polymer ratio | quantity of DEET applied (g) | time to no detectable odor (hr) |
|---|---|---|---|---|---|
| 5 | 0 | 0 | 100% DEET | .15 | 30.5 |
| 5 | .5 | 92 | 10:1 | .005 | 18 |
| 5 | 5 | 84 | 1:1 | .005 | 18 |
| 2.5 | 5 | 92 | .5:1 | .0025 | 18 |
| 1.25 | 5 | 92 | .25:1 | .0013 | 30.5 |

This shows that the presence of the polymer in the formulation retards the evaporation of the DEET. A formulation containing polymer and 0.0013 g of DEET retained its activity as long as a formulation which contained 0.15 g of DEET but no polymer.

EXAMPLE 8

A formula based on PVP/eicosene.

The following ingredients were prepared and agitated with a propeller stirrer. Solution A was prepared and heated to 80° C. and the mixture was allowed to cool to 40° C. and Solution B was added and the whole was allowed to cool to room temperature with continued agitation.

| | grams added | percent concentration |
|---|---|---|
| (A) DC 345 | 7.4 | 6.57 |
| polyvinylpyrrolidone/eicosene copolymer | 5.7 | 5.06 |
| DC 3225C | 4.6 | 4.09 |
| DEET | 10.0 | 8.88 |
| (B) Deionized water | 80.0 | 71.05 |
| Carbopol 940 | 0.8 | .71 |
| Pluracare L-64 | 2.9 | 2.58 |
| after thorough mixing add | | |
| triethanolamine | 0.1 | 0.09 |
| (C) methyl paraban/propyl paraban/ diazolidinyl urea in propylene glycol (1:1:2:6) | 1.1 | 0.97 |
| EDTA | .088 | 0.08 |

This formula was equal in efficacy to that of the 100% DEET solution in field conditions.

In the test described in Example 2, this formula was superior in lack of skin penetration as indicated by no reaction in the human volunteer.

Since the above disclosure is subject to variations, it should be understood that the above examples are merely illustrative and that the invention disclosed herein should be limited only by the claims.

We claim:

1. A composition having slow release properties for an insect repellent consisting essentially of a polymer consisting of polyvinyl pyrrolidone and an alkyl group of 4–30 carbons, said polymer formulated in a suitable formulation with a volalite insect repellent.

2. The composition of claim 1 wherein the alkyl group is hexadecene, eicosene or a 1-triacontene.

3. The composition of claim 1 wherein the alkyl group is hexadecene.

4. The composition of claim 1 wherein the alkyl group is eicosene.

5. The composition of claim 1 wherein the alkyl group is 1-triacontene.

6. The composition of claim 1 wherein the insect repellent is ethyl hexanediol.

7. A method for repelling insects, consisting essentially of applying a volatile insect repellent composition to an area to be made repellent, said composition having enhanced residual insect repellent activity and consisting essentially of:

(1) at least one volatile insect repellent; and (2) an effective amount of at least one polymer for increasing the residual activity of the volatile insect repellent, said polymer consisting of:

(a) polyvinylpyrrolidone, and (b) an alkyl group having 4–30 carbon atoms.

8. The method of claim 7 wherein the alkyl group is hexadecene, eicosene or 1-triacontene.

9. The method of claim 7 wherein the alkyl group is hexadecene.

10. The method of claim 7 wherein the alkyl group is eicosene.

11. The method of claim 7 wherein the alkyl group is 1-triacontene.

12. The method of claim 7 wherein the insect repellent is N,N-diethyl toluamide.

* * * * *